(12) United States Patent
Yamada et al.

(10) Patent No.: US 10,206,815 B2
(45) Date of Patent: Feb. 19, 2019

(54) INJECTOR FOR INTRAOCULAR LENS

(71) Applicant: Santen Pharmaceutical Co., Ltd., Osaka-shi, Osaka (JP)

(72) Inventors: Yoshitaka Yamada, Osaka (JP); Katsuyuki Ueno, Osaka (JP); Takashi Tanaka, Osaka (JP)

(73) Assignee: Santen Pharmaceutical Co., Ltd, Osaka (JP)

( * ) Notice: Subject to any disclaimer, the term of this patent is extended or adjusted under 35 U.S.C. 154(b) by 316 days.

(21) Appl. No.: 15/112,840

(22) PCT Filed: Feb. 20, 2015

(86) PCT No.: PCT/JP2015/054730
§ 371 (c)(1),
(2) Date: Jul. 20, 2016

(87) PCT Pub. No.: WO2015/125905
PCT Pub. Date: Aug. 27, 2015

(65) Prior Publication Data
US 2016/0331587 A1 Nov. 17, 2016

(30) Foreign Application Priority Data
Feb. 20, 2014 (JP) .................................. 2014-030556

(51) Int. Cl.
*A61F 2/16* (2006.01)
*A61F 9/00* (2006.01)

(52) U.S. Cl.
CPC .......... *A61F 9/0017* (2013.01); *A61F 2/1678* (2013.01); *A61F 2002/1681* (2013.01)

(58) Field of Classification Search
CPC ....................................... A61F 2/1662–2/1678
(Continued)

(56) References Cited

U.S. PATENT DOCUMENTS

| 2005/0277944 A1 | 12/2005 | Kappelhof et al. |
| 2007/0270881 A1 | 11/2007 | Hishinuma et al. |

(Continued)

FOREIGN PATENT DOCUMENTS

| EP | 1424048 | 6/2004 |
| EP | 2072025 A1 | 6/2009 |

(Continued)

OTHER PUBLICATIONS

Extended European search report dated Oct. 13, 2017 for European Patent Application No. 15751870.5, 7 pages.

*Primary Examiner* — Kathleen Holwerda
(74) *Attorney, Agent, or Firm* — Squire Patton Boggs (US) LLP

(57) ABSTRACT

The purpose of the present invention is to provide an injector for an intraocular lens, whereby it is possible to easily set a lens support part to an appropriate position on a lens holder, and to safely carry out insertion work. A lens holder (404) is provided with a base part (441), a release-side guide part (442), and a passing part (443). A concave part (450) for housing the tip of a first lens support part (92) is formed on the release-side guide part (442). The concave part (450) holds the first lens support part (92) above the passing part (443). The release-side guide part (442) guides the first lens support part (92) along the circumference of an optical part (91).

7 Claims, 10 Drawing Sheets

(58) Field of Classification Search
USPC .......................................... 623/6.12; 606/107
See application file for complete search history.

(56) References Cited

U.S. PATENT DOCUMENTS

| | | | |
|---|---|---|---|
| 2008/0058830 A1* | 3/2008 | Cole | A61F 2/1664 |
| | | | 606/107 |
| 2009/0318933 A1 | 12/2009 | Anderson | |
| 2010/0130985 A1 | 5/2010 | Tanaka | |
| 2011/0190777 A1 | 8/2011 | Hohl | |
| 2012/0221102 A1 | 8/2012 | Tanaka et al. | |
| 2014/0135782 A1* | 5/2014 | Valle | A61F 2/1691 |
| | | | 606/107 |
| 2014/0228856 A1 | 8/2014 | Niwa et al. | |

FOREIGN PATENT DOCUMENTS

| | | |
|---|---|---|
| EP | 2491902 A1 | 8/2012 |
| JP | 2004-173805 | 6/2004 |
| JP | 2007-307082 | 11/2007 |
| JP | 2009-153915 | 7/2009 |
| JP | 2012-502700 | 2/2012 |
| JP | 2013-244186 | 12/2013 |
| WO | WO 2008/029498 | 3/2008 |
| WO | WO 2011/048631 | 4/2011 |
| WO | WO 2013/038687 | 3/2013 |

* cited by examiner

INJECTOR FOR INTRAOCULAR LENS

TECHNICAL FIELD

The present invention relates to an injector for an intraocular lens that releases an intraocular lens set in a lens holder by pushing out by way of a plunger.

BACKGROUND ART

Conventionally, in cataract surgery in which a clouded crystalline lens in the eye is replaced with an artificial intraocular lens, in order to make the incision smaller, a method of inserting the intraocular lens into the eye in a folded state has been known. An injector for an intraocular lens is used in the operation to fold and insert this intraocular lens into the eye. There is Patent Document 1 as an example disclosing this type of injector for an intraocular lens. Patent Document 1 discloses the following configuration for an intraocular lens insertion instrument for inserting an intraocular lens into the eye. In other words, the intraocular lens insertion instrument includes: an outer cylinder including an insertion part that inserts into an incision formed in the eyeball; a push-out means for pushing out the intraocular lens housed inside the outer cylinder to be able to advance/retract through an insertion part into the eye; a friction producing member that is placed so as to contact the push-out means, and producing a frictional force on the push-out device; and an adjustment member that is installed inside the outer cylinder, pressurizes the friction producing member from the axial direction of the push-out means, and adjusts a force pushing out according to a change in rotation angle relative to the axial direction of the push-out means.
Patent Document 1: Japanese Unexamined Patent Application, Publication No. 2004-173805

DISCLOSURE OF THE INVENTION

Problems to be Solved by the Invention

As also shown in Patent Document 1, the intraocular lens inserted into the eye includes an optical part and a lens support part that supports this optical part inside the eye. This type of intraocular lens is inserted into the eye by pushing out in a start bending the leading end of the lens support part to the optical part side. In order for the lens support part to be pushed out in such as state, it is necessary to perform a setting operation so that the lens support part is at a predetermined position on the lens holder, when setting the intraocular lens in the lens holder. This is because, in the case of performing the insertion operation in a state in which the lens support part is not at the predetermined position on the lens holder, insertion to the eye may be done wrong, and the lens support part may be damaged. However, since the lens support part is very small, the operation of accurately setting the lens support part at the above-mentioned predetermined position using an instrument such as tweezers requires an exceedingly long time, and depending on the way of setting, the lens support part may not be at the predetermined position. In this point, there has been margin for improvement in the configuration disclosed in Patent Document 1 from the viewpoint of simplification of the setting operation of the intraocular lens to the lens holder and an increase in safety.

Therefore, the present invention has an object of providing an injector for an intraocular lens that enables setting the lens support part at the appropriate position on the lens holder easily, and enables performing the insertion operation more safely.

Means for Solving the Problems

The present invention relates to an injector for an intraocular lens that releases an intraocular lens, having an optical part that is set in a lens holder and a lens support part extending from the optical part, by pushing out by way of a plunger, in which the lens holder includes: a base part having a placement part on which the optical part is placed; a release-side guide part that is disposed at a placement face side of the base part on which the optical part is placed, which is a side releasing the intraocular lens, and guides the lens support part so as to run along a circumference of the optical part; and a passing part formed between the placement face and a bottom face of the release-side guide part to allow the optical part to pass therethrough.

It is preferable for a concave part that accommodates a leading end of the lens support part to be formed in the release-side guide part.

It is preferable for the release-side guide part to retain the lens support part upwards from the passing part by way of the concave part.

It is preferable for the lens holder to further include: a through hole that is formed at the periphery of the placement part of the base part so as to run along an outer circumference of the optical part; and a rotating part having a basal part and a projecting part that projects from the basal part, being disposed on a surface opposite to the placement face of the base part so that the projecting part can inserted and removed from the through hole, and being able to rotate so that the projecting part moves along the through hole, in which the through hole is formed so that at least a part thereof is disposed between the placement part and the release-side guide part, and when viewed in a pushing direction of the plunger, the projecting part inserted in the through hole can move from a setting initial position overlapping with the release-side guide part until a setting end position not overlapping with the release-side guide part, and in which the release-side guide part, when the projecting part in a state sandwiched between the optical part and the lens support part moves from the setting initial position to the setting end position, guides the lens support part at the setting end position so as to run along the circumference of the optical part.

It is preferable for the release-side guide part to have a retaining part that is disposed more to a side of the placement part than a position at which the passing part is disposed in the pushing direction of the plunger, and retains the lens support part at a position separated from the placement face at the setting initial position.

It is preferable for the release-side guide part to have a sloped part that is disposed at a position overlapping the passing part in a thickness direction of the base part, and slopes to a side of the placement part as approaching the passing part in the thickness direction.

It is preferable for the release-side guide part to be disposed so as not to overlap with a leading-end portion of the plunger when viewed in the pushing direction of the plunger.

It is preferable for the intraocular lens to have a second lens support part that is disposed so as to be point symmetrical with a center of the optical part as the center of symmetry relative to the lens support part, and the lens holder to further include a plunger-side guide part that is disposed at an opposite side to a placement face side of the base part on which the optical part is placed, which is a side releasing the intraocular lens, and guides the second lens support part so as to run along the circumference of the optical part.

Effects of the Invention

According to the injector for an intraocular lens of the present invention, it is possible to easily set the lens support part at an appropriate position on the lens holder, and it is possible to perform the insertion operation more safely.

PREFERRED MODE FOR CARRYING OUT THE INVENTION

Hereinafter, each preferred embodiment of an injector for an intraocular lens of the present invention will be explained while referencing the drawings. First, the overall configuration of an injector 1 for an intraocular lens according to a first embodiment of the present invention will be explained.

Figure 1:
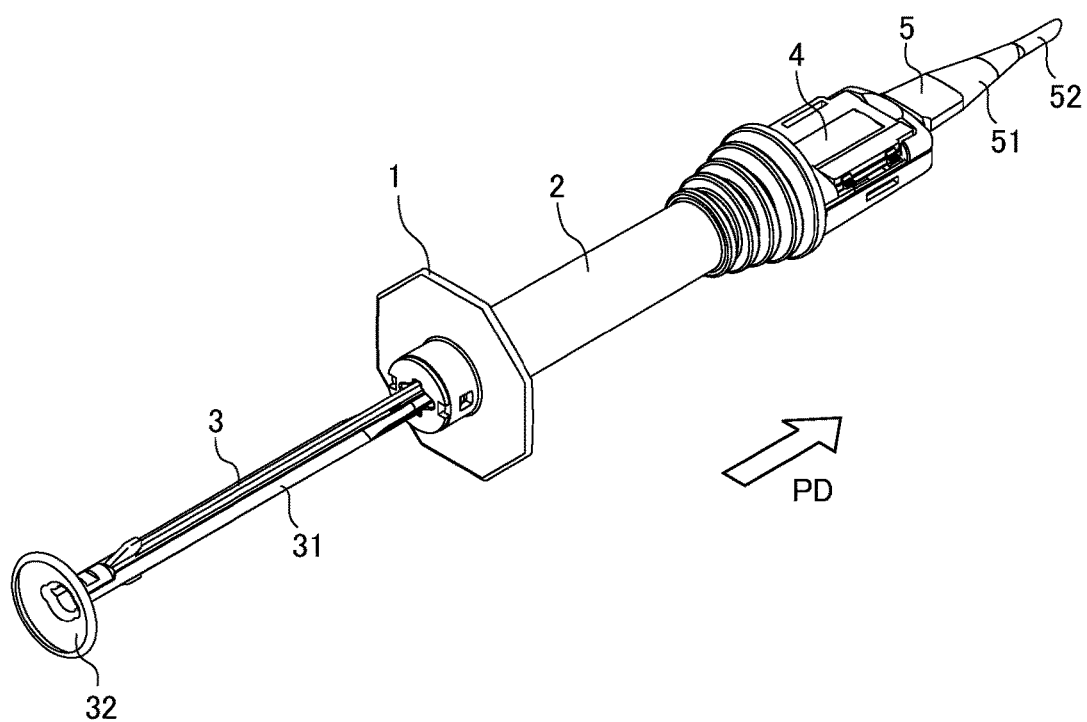
FIG. 1 is a perspective view showing an appearance of an injector for an intraocular lens of a first embodiment.

As shown in FIG. 1, the injector 1 for an intraocular lens includes a main body 2, a plunger 3, a lens holder 4, and a leading end tip 5. This injector 1 for an intraocular lens is an insertion instrument for an intraocular lens 90 (refer to FIG. 6) set in the lens holder 4 with a plunger 3 to release intraocular from the leading-end tip 5. It should be noted that, in the following explanation, the pushing direction PD indicates the same direction as the axial direction of the plunger 3, and a release side indicates a side at which the intraocular lens 90 is released in the pushing direction PD. In addition, the orientation of the outlined arrow in the drawings used in the following explanation shall indicate the release side in the pushing direction PD.

Figure 6:
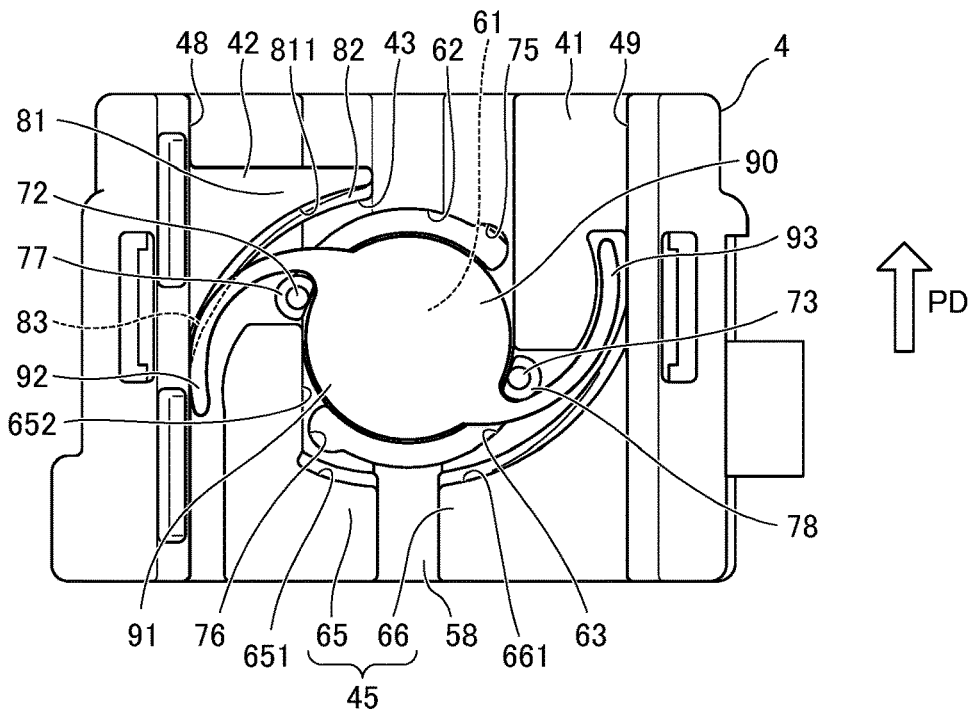
FIG. 6 is a plan view showing an aspect of an intraocular lens and the lens holder at a setting initial position.

In addition, the intraocular lens 90 of the following configuration is used with the injector 1 for an intraocular lens of the first embodiment. The intraocular lens 90 includes an optical part 91, a first lens support part 92, and a second lens support part 93 (refer to FIG. 6). The optical part 91 is a lens portion functioning as the crystalline lens after intraocular insertion. The first lens support part 92 and second lens support part 93 are formed so as to extend in a curved shape from a lateral face of the optical part 91, and achieve a function of retaining the optical part 91 inside the eye after intraocular insertion. As shown in FIG. 6, the first lens support part 92 and second lens support part 93 are arranged as to be in a point symmetrical positional relationship with the center of the optical part 91 as the center of symmetry. This optical part 91, first lens support part 92 and second lens support part 93 are formed to be deformable from materials having flexibility. It should be noted that, in the present embodiment, a single piece type in which the optical part 91, first lens support part 92 and second lens support part 93 are integrally molded is explained as an example.

Next, each configuration of the injector 1 for an intraocular lens will be explained. The main body 2 of the injector 1 for an intraocular lens is formed in a hollow cylindrical shape. The plunger 3 is inserted into this hollow portion to be movable in the pushing direction PD.

The plunger 3 includes a shaft part 31 and a pressing part 32. The shaft part 31 is formed in a spindle shape, and the leading end side thereof is plugged into the hollow portion of the main body 2. The pressing part 32 is formed in a flanged shape, and is arranged at an end of the shaft part 31 on a side not plugged into the main body 2. When the user of the injector 1 for an intraocular lens pushes the pressing part 32 to the side of the main body 2, the leading end of the shaft part 31 moves so as to push out the intraocular lens 90 on the lens holder 4 to a release side.

The lens holder 4 is arranged between the main body 2 and the leading-end tip 5 in the pushing direction PD, and is configured to be able to set the intraocular lens 90 inside. The inside of the lens holder 4 is in communication with the inside of the leading-end tip 5, whereby movement of the intraocular lens 90 from the lens holder 4 to the leading-end tip 5 is made possible. It should be noted that the detailed configuration of this lens holder 4 will be described later.

The leading-end tip 5 includes a nozzle part 51 and a release part 52. The nozzle part 51 has an internal channel communicating with the lens holder 4, and this internal channel is configured so as to narrow as progressing to the release side. The release part 52 is a release opening for releasing the intraocular lens 90 to outside of the injector 1 for an intraocular lens, and is positioned at the leading end of the injector 1 for an intraocular lens. The intraocular lens 90 passing through the nozzle part 51 is pushed to the inner wall of the internal channel, and when seen in the pushing direction PD, the optical part 91 will be gradually folded so as to form a valley folded shape. The intraocular lens 90 is released from the release part 52 into the eye in a state in which the optical part 91 is folded in this way. It should be noted that the lens holder 4 or leading-end tip 5 of the present embodiment is configured so as to be able to inject an appropriate viscoelastic material or wound treatment drug such as sodium hyaluronate, hydroxypropyl methylcellulose and polyvinyl pyrrolidone.

Figure 2:
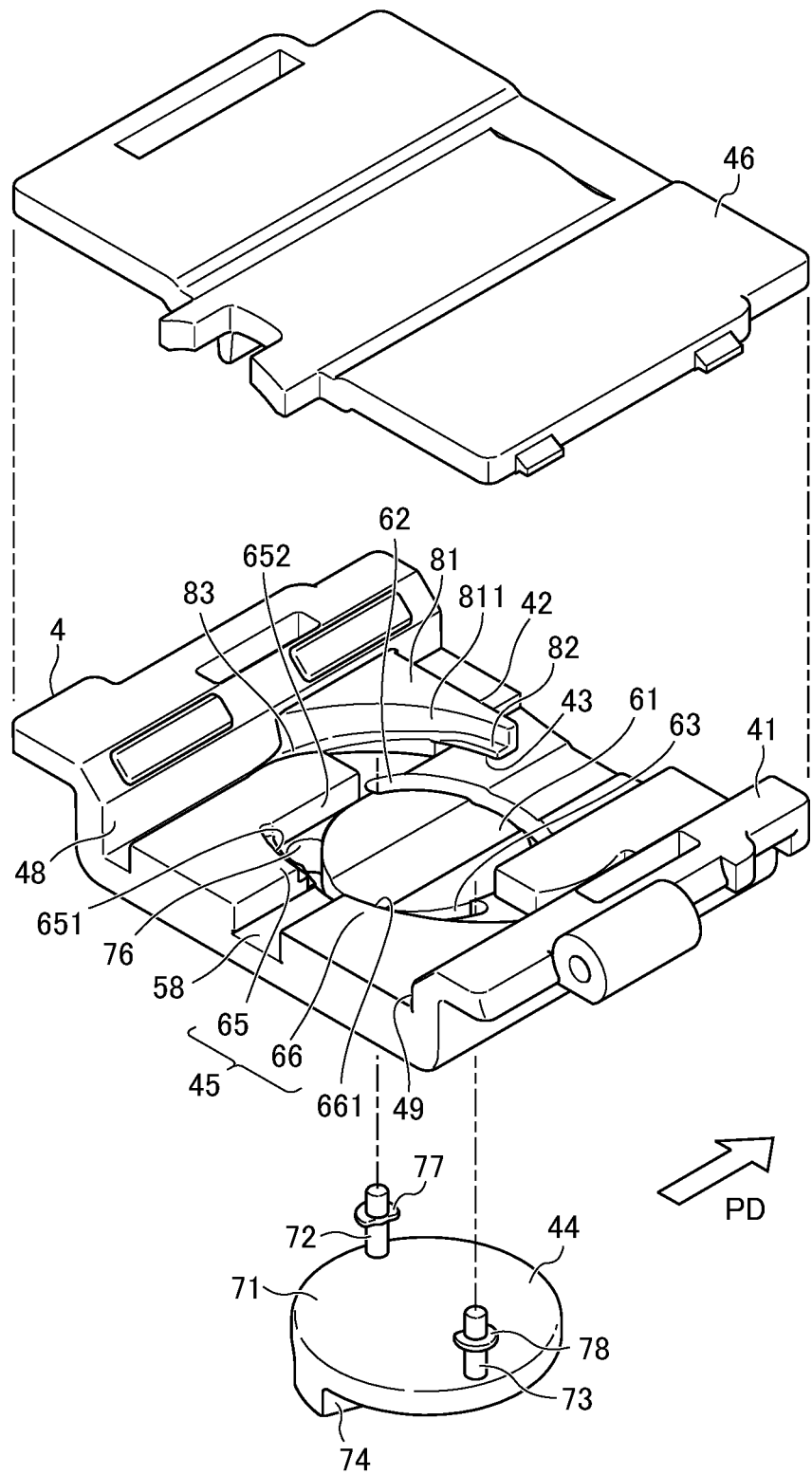
FIG. 2 is an exploded perspective view showing a lens holder of a first embodiment.
Figure 3:
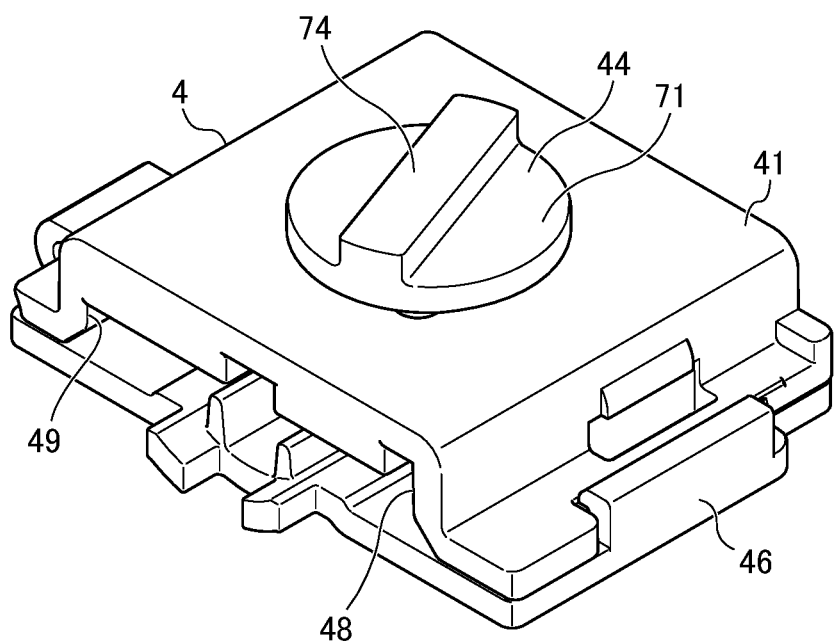
FIG. 3 is a perspective view showing a bottom face side of the lens holder of the first embodiment.
Figure 4:
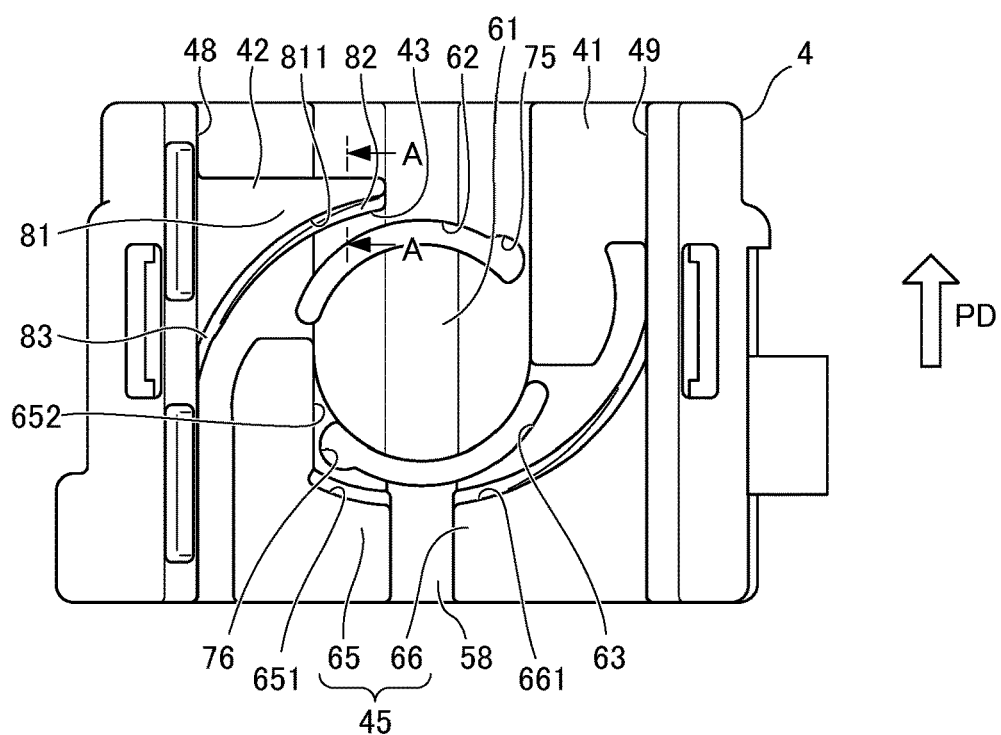
FIG. 4 is a plan view showing the inside of the lens holder of the first embodiment.

Next, the detailed configuration of the lens holder 4 will be explained. FIG. 2 is an exploded perspective view showing the lens holder 4. FIG. 3 is a perspective view showing a bottom surface side of the lens holder 4. FIG. 4 is a plan view showing the inside of the lens holder 4.

As shown in FIG. 2, the lens holder 4 of the present embodiment includes: a base part 41, a release-side guide part 42, a passing part 43, a plunger-side guide part 45, a rotating part 44, and a cover 46. It should be noted that, in the following explanation of the lens holder 4, the vertical direction indicates the same direction as the thickness direction of the base part 41 (or thickness direction of the optical part 91 placed on a placement part 61). In addition, the left/right direction indicates a direction orthogonal to the vertical direction when viewing the lens holder 4 in the pushing direction PD, and one side and another side in this left/right direction will be explained as left/right in the case of orienting the release side in the pushing direction PD. Furthermore, the opposite side to the release side of the base part 41 will be explained as a main body 2 side of the base part 41.

The base part 41 is formed in a substantially plate shape, and includes the placement part 61, a first through hole 62 and a second through hole 63 as through holes, a plunger passing part 58, and outer walls 48 and 49.

The placement part 61 is arranged at the center of the base part 41, and is a portion at which the optical part 91 of the intraocular lens set in the lens holder 4 is placed.

The first through hole 62 and the second through hole 63 are arranged at the circumference of the placement part 61, and are formed in circular arcs along the outer circumference of this placement part 61. When placing the optical part 91 on the placement part 61, the first through hole 62 and the second through hole 63 are configured so as to run along the outer circumference of this optical part 91 (refer to FIGS. 6 and 7).

The first through hole 62 is arranged on a release side of the base part 41. As shown in FIG. 4, the first through hole 62 is formed so that an end on the left side thereof in a plan view is positioned between the placement part 61 and the release-side guide part 42, and the end on the right side is positioned more to the right side than the release-side guide part 42. In addition, a pullout part 75 that is a hole larger than the width of the first through hole 62 is arranged at an end on the right side of the first through hole 62. This pullout part 75 is for pulling out a first projecting part 72 of the rotating part 44 described later from the first through hole 62.

The second through hole 63 is the same shape as the first through hole 62, and is arranged on the main body 2 side of the base part 41 so as to face each other by sandwiching the placement part 61. A pullout part 76 that is a hole larger than the width of the second through hole is arranged at an end on the left side of the second through hole 63. This pullout part 76 is for pulling out a second projecting part 73 described later from the second through hole 63.

The plunger passing part 58 is arranged on a main body 2 side of the base part 41. The plunger passing part 58 constitutes a pass-through channel for the leading end portion of the plunger 3 to pass through, and is formed so that a clearance with the plunger 3 becomes smaller in order to restrict the deviation in the left/right direction of the plunger 3.

The outer wall 48 is arranged on the left side (one side) of the base part 41, and the outer wall 49 is arranged at the right side (other side). The outer walls 48 and 49 are formed so as to separate the inside and outside of the lens holder 4 at the placement surface side of the base part 41 at which the optical part 91 is placed.

As shown in FIG. 2, the release-side guide part 42 is a top face of the base part 41 (same face as the face at which the placement part 61 is arranged), and is arranged on the release side of the base part 41. The release-side guide part 42 includes a release-side guide main body 81, sloped part 82 and retaining part 83.

As shown in FIG. 4, the release-side guide main body 81 has curved face 811 that curves in a plan view to the right side while heading towards the release side from the vicinity of the center of a lateral face of the outer wall 48 on the left side. The curved face 811 of this release-side guide main body 81 is arranged so as face the placement part 61 by sandwiching the first through hole 62, as well as follow this first through hole 62. In addition, the curved face 811 of the release-side guide main body 81 does not overlap with the pass-through channel of the plunger 3, and is configured so that a leading end thereof is positioned at a near side of the pass-through channel of the plunger 3.

Figure 5:
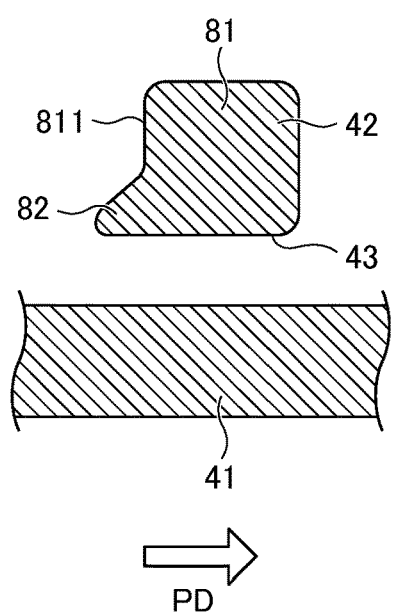
FIG. 5 is a schematic profile along the line A-A in FIG. 4.

FIG. 5 is a schematic profile along the line A-A in FIG. 4. FIG. 5 schematically expresses a state viewing, from the right side, an aspect of a cross section in the vicinity of a right-side end of the release-side guide part 42. As shown in FIG. 5, the curved face 811 of the release-side guide main body 81 is configured to be substantially parallel to the vertical direction (thickness direction of the base part 41) in a lateral side view.

As shown in FIG. 5, the sloped part 82 is arranged at a lower part of the curved face 811 of the release-side guide main body 81. The sloped part 82 is formed so as to slope so as to be distanced from the release-side guide main body 81 as advancing downwards, and becomes a shape projecting to the placement part 61 side as approaching the top face of the base part 41.

As shown in FIG. 4, the retaining part 83 is arranged in the vicinity of the center of the outer wall 48 on the left side. The retaining part 83 is formed so as to project from the top face of the base part 41, and the top face of this retaining part 83 is higher than the placement surface. In addition, a position of the top face of the retaining part 83 is set to be lower than the height of the curved face 811 of the release-side guide main body 81 and the sloped part 82. Then, the retaining part 83 is configured so as to form a gentle upslope towards the release side, and is connected to the release-side guide main body 81.

The passing part 43 is below the release-side guide main body 81 and sloped part 82, and is arranged in a channel through which the optical part 91 of the intraocular lens 90 passes. The passing part 43 of the present embodiment is configured so that the left side of the optical part 91 passes through this passing part 43 when the intraocular lens 90 modes from the lens holder 4 to the leading-end tip 5 (refer to FIG. 8). As shown in FIG. 5, the passing part 43 of the present embodiment is formed in a gap between the bottom face of the release-side guide part 42 and the top face of the base part 41.

The plunger-side guide part 45 is a top face of the base part 41, and is arranged on a main body 2 side thereof. The plunger-side guide part 45 includes a base-end side guide part 65 and leading-end side guide part 66. The base-end side guide part 65 and leading-end side guide part 66 are for guiding a second lens support part 93 of the intraocular lens 90 at a main body 2 side of the base part 41, and are arranged in the vicinity of the plunger passing part 58. The base-end side guide part 65 is arranged on the left side of the plunger passing part 58, and the leading-end side guide part 66 is arranged on the right side of the plunger passing part 58.

The base-end side guide part 65 has a curved face 651 that curves to the release side while heading from the plunger passing part 58 towards the outer wall 48 on the left side. The curved face 651 of the base-end side guide part 65 faces a side of the placement part 61 by sandwiching the second through hole 63 therewith in a plan view, and is formed so as to follow a part on the left side of the second through hole 63. The end on the left side of the second through hole 63 is positioned between the placement part 61 and the base-end side guide part 65. In addition, the base-end side guide part 65 has a lateral face 652 extending in the pushing direction PD, and is made to be able to retain the base end side of the second lens support part 93 at a setting end position described later by the lateral face 652 (refer to FIG. 7).

The leading-end side guide part 66 has a curved face 661 that curves to the release side while heading towards the outer wall 49 on the right side from the plunger passing part 58. The curved face 661 of the leading-end side guide part 66 is also formed so as to face a side of the placement part 61 by sandwiching the second through hole 63 therewith in a plan view, and follow a part on the right side of the second through hole 63. The end on the right side of the second through hole 63 is positioned between the placement part 61 and the leading-end side guide part 66. In addition, the curved face 651 of the base-end side guide part 65 and the curved face 661 of the leading-end side guide part 66 of the present embodiment are both formed to be substantially parallel in the thickness direction of the base part 41.

Next, the rotating part 44 will be explained. As shown in FIG. 2, the rotating part 44 includes a basal part 71, a first projecting part 72, a second projecting part 73, and an operating part 74. The basal part 71 is formed in a disk shape, and from a surface on one side thereof, the first projecting part 72 and second projecting part 73 project in rod shapes. The first projecting part 72 and second projecting part 73 are arranged so as to face each other sandwiching the center of the basal part 71. A flange part 77 is arranged in the vicinity of a leading end of the first projecting part 72, and a flange part 78 is arranged in the vicinity of a leading end of the second projecting part 73. As shown in FIG. 3, the operating part 74 is arranged at an opposite surface to the surface from which the first projecting part 72 and second projecting part 73 project. The operating part 74 is formed so as to project from the opposite surface.

The diameter of the first projecting part 72 is set to be smaller than the width of the aforementioned first through hole 62, and the diameter of the flange part 77 is set so as to be larger than the width of the first through hole 62 and smaller than the size of the pullout part 75. Similarly, the diameter of the second projecting part 73 is set to be smaller than the width of the second through hole 63, and the diameter of the flange part 78 is set to be larger than the width of the second through hole 63, and smaller than the size of the pullout part 76. The first projecting part 72 and second projecting part 73 are thereby able to be put through the pullout parts 75 and 76 into the first through hole 62 and second through hole 63, respectively.

When rotating the rotating part 44 in a state putting the first projecting part 72 and second projecting part 73 into the pullout parts 75 and 76, respectively, it is configured so that the first projecting part 72 moves following the first through hole 62, and the second projecting part 73 moves following the second through hole 63. In this way, the rotating part 44 is installed rotatably to an opposite surface (bottom face of the base part 41) to the placement face on which the placement part 61 is placed, in a state in which the first projecting part 72 is put into the first through hole 62 and the second projecting part 73 is put into the second through hole 63. It should be noted that the first projecting part 72 and second projecting part 73 are prevented from falling out from the first through hole 62 and second through hole 63 by the flange parts 77 and 78 other than the pullout parts 75 and 76, respectively.

The cover 46 is installed to be closable to the base part 41, and is formed so as to cover the top face of the base part 41 in a state in which this cover 46 is closed. The cover 46 has a restricting part (omitted from illustrated) for restricting the movement in the vertical direction of the intraocular lens 90. When closing the cover 46 in a state setting the intraocular lens 90 in the lens holder 4, the movement of the intraocular lens 90 in the vertical direction is suppressed by this restricting part.

Figure 7:
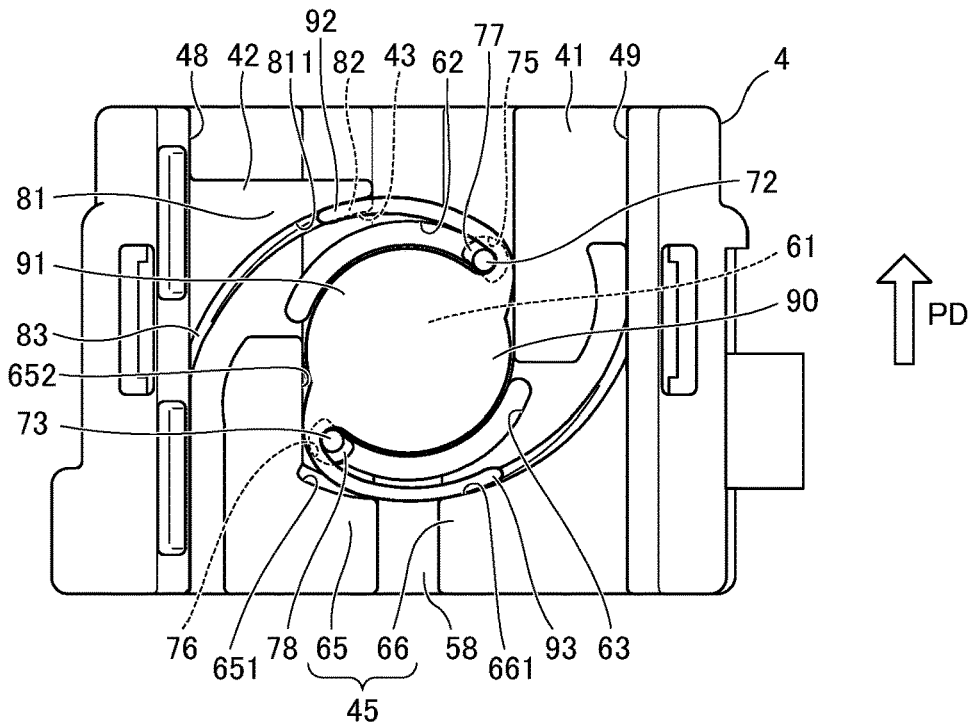
FIG. 7 is a plan view showing an aspect of an intraocular lens and the lens holder at a setting end position.

Next, the setting operation of the intraocular lens 90 to the lens holder 4 will be explained. FIG. 6 is a plan view showing an aspect of the intraocular lens 90 and lens holder 4 at a setting initial position. FIG. 7 is a plan view showing an aspect of the intraocular lens 90 and lens holder 4 at a setting end position.

As shown in FIG. 6, first, the rotating part 44 is set so that the first projecting part 72 is positioned at an end on the left side of the first through hole 62, and the second projecting part 73 is positioned at an end on the right side of the second through hole 63. This state is the setting initial position of the rotating part 44. It should be noted that, when the rotating part 44 is at the setting initial position, the first projecting part 72 is at a position overlapping with the release-side guide part 42 in the pushing direction PD, and the second projecting part 73 is at a position not overlapping with the release-side guide part 42.

The setting operation of the intraocular lens 90 to the lens holder 4 is performed in a state in which the rotating part 44 is at the setting initial position. More specifically, it enters a state sandwiching the first projecting part 72 by the first lens support part 92 and a lateral face of the optical part 91, and enters a state sandwiching the second projecting part 73 by the second lens projecting part 93 and a lateral face of the optical part 91. At this time, since it is possible to set the intraocular lens 90 with the first projecting part 72 and second projecting part 73 as landmarks, a user can easily perform an operation to place the first lens support part 92 and second lens support part 93 at the setting initial position of the lens holder 4. After this operation, an operation to make the rotating part 44 move to the setting end position by closing the cover 46 is performed.

As shown in FIG. 6, the first lens support part 92 at the setting initial position enters a state in which a part on the leading-end side thereof is supported from below by the retaining part 83. As mentioned previously, since the retaining part 83 projects from the top face of the base part 41, a part on the leading-end side of the first lens support part 92 at the setting initial position comes to be retained at a position more upwards from the top face of the base part 41.

Next, the behaviors of the rotating part 44 and intraocular lens 90 when the rotating part 44 rotates from the setting initial position shown in FIG. 6 to the setting end position shown in FIG. 7 will be explained. When the rotating part 44 starts to rotate from the setting initial position to the setting end position, the first projecting part 72 contacts the base-end side of the first lens support part 92, and the second projecting part 73 contacts the base-end side of the second lens support part 93. Accompanying rotation of the rotating part 44, the first projecting part 72 causes a force to rotate clockwise to act on the lens support part 92, and the second projecting part 73 causes a force to rotate clockwise to act on the second lens support part 93. According to this action, the intraocular lens 90 starts to rotate on the placement part 61. When the first projecting part 72 moves until the end on the right side of the first through hole 62 (pullout part 75), and the second projecting part 73 moves until the end on the left side of the second through hole 63 (pullout part 76), movement more than this is restricted by the end faces of the first through hole 62 and second through hole 63, and this position becomes the setting end position. As shown in FIG. 7, it is understood from the setting end position that, when viewing in the pushing direction PD, the first projecting part 72 moves to a position not overlapping with the release-side guide part 42, and the second projecting part 73 moves to a position overlapping with the release-side guide part 42.

The first lens support part 92 moves following the rotation of the rotating part 44 while contacting the curved face 811 of the release-side guide main body 81 and the sloped part 82. The sloped part 82 guides the first lens support part 92 so as to head upwards according to this slope. As mentioned above, a part of the leading-end side of the first lens support part 92 is retained at a position higher than the top face of the base part 41 by the retaining part 83. Since the first lens support part 92 moves by making the slope of the retaining part 83 rise from a position higher than the placement face, running on the sloped part 82 is also carried out smoothly. At this time, even in a case of making movement whereby the first lens support part 92 tries to penetrate the passing part 43, this movement is restricted by the sloped part 82. When the rotating part 44 rotates until the setting end position, the base-end side of the first lens support part 92 separates from the release-side guide part 42; however, the leading-end side thereof is maintained in a state remaining in contact with the release-side guide part 42.

In addition, with the first lens support part 92 at the setting end position, the leading-end side thereof is retained upwards from the passing part 43 by the release-side guide main body 81 and sloped part 82. The first lens support part 92 can be considered to be made to displace the position thereof upwards when moving from the setting initial position to the setting end position by way of the release-side guide part 42. In addition, as shown in FIG. 7, with the first lens support part 92 in this state, the leading end thereof reaches a position closer to the optical part 91 compared to a state not contacting the release-side guide part 42, and is curved in a shape running along the outer circumference of the circular optical part 91.

The second lens support part 93 contacts the curved face 661 of the leading-end side guide part 66 from the base-end side thereof when the rotation starts. A part on the base-end side of the second lens support part 93 separates from the leading-end side guide part 66 when having moved to the flange passing part 58, and subsequently, moves up to the setting end position while being guided on the curved face 651 of the base-end side guide part 65. The leading-end side of the second lens support 93 enters a state contacting the leading-end side guide part 66 after the base-end side, and a part of the leading-end side is retained by the leading-end side guide part 66 at the setting end position. In addition, as shown in FIG. 7, with the second lens support part 93 in this state, the leading end thereof reaches a position closer to the optical part 91 compared to a state not contacting the base-end side guide part 65 and leading-end side guide part 66, and is curved in a shape running along the outer circumference of the circular optical part 91.

As shown above, the lens holder 4 of the present embodiment can cause the first lens support part 92 and second lens support part 93 to mechanically move to a position appropriately retained, by way of rotation of the rotating part 44. In this state, as mentioned above, the setting operation is completed by pulling out the first projecting part 72 and second projecting part 73 from the pullout part 75 (first through hole 62) and pullout part 76 (second through hole 63), respectively, and removing the rotating part 44 from the base part 41.

Figure 8:
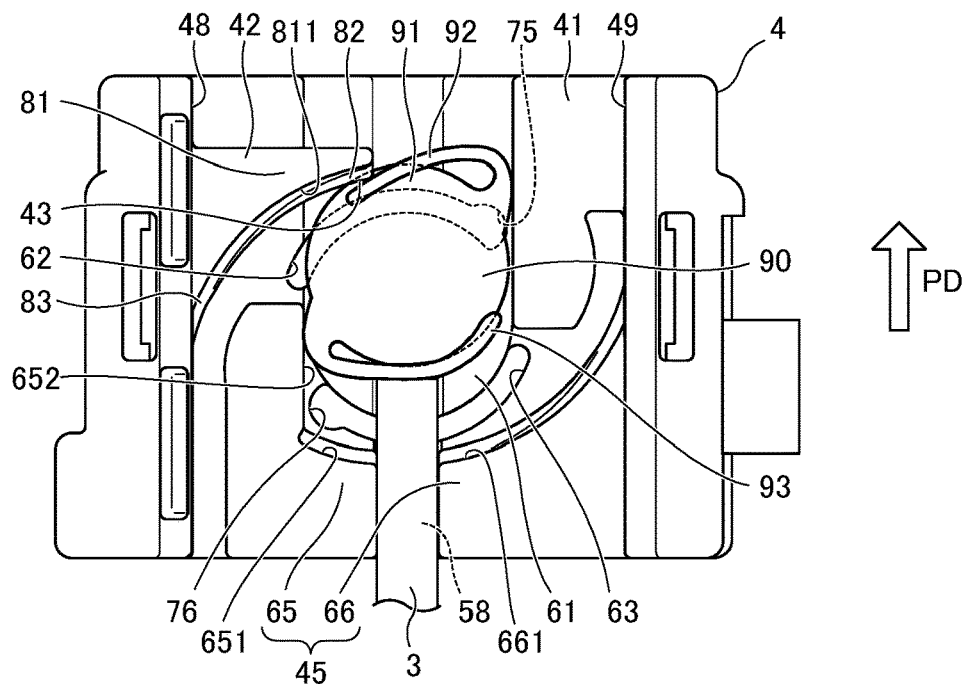
FIG. 8 is a plan view showing an aspect of the lens holder when the ocular lens is pushed out.

Next, the pushing operation of the plunger 3 will be explained. FIG. 8 is a view showing an aspect of the lens holder 4 when the intraocular lens 90 is pushed.

After setting operation completion, when pushing the plunger 3 into the side of the main body 2, the leading end of the plunger 3 contacts the second lens support part 93 and optical part 91. At this time, the leading-end side of the second lens support part 93, due to being retained in a state curved to the side of the optical part 91, can prevent a situation where appropriate contact with the plunger 3 is hindered, by the leading end of the second lens support part 93 being positioned at the plunger passing part 58.

As shown in FIG. 8, the intraocular lens 90 receiving the pressure force of the plunger 3 moves to a pushed out side, and a part on the left side of the optical part 91 starts to pass through the passing part 43. At this time, the leading-end side of the first lens support part 92 will remain in contact with the curved face 811 of the release-side guide main body 81 and the sloped part 82. When the optical part 91 advances further to the release side from the state of FIG. 8, although deforming, a portion of the first lens support part 92 contacting with the release-side guide part 42 moves from the base-end side to the leading-end side, and eventually separates from the release-side guide part 42. At this moment, the intraocular lens 90 moves sufficiently to the side of the leading-end tip 5, and even after separating from the release-side guide part 42, the first lens support part 92 advances further to the release side while the movement thereof is appropriately restricted by the inner wall of the leading-end tip 5. As mentioned above, at the inside of the leading-end tip 5, the optical part 91 is folded in a valley folded shape by the inner wall thereof. The first lens support part 92 is led so that the leading end thereof is positioned above the optical part 91 by the inner wall of the leading-end tip 5. As mentioned above, the first lens support part 92 is supported upwards from the placement face by the release-side guide part 42; therefore, the movement to above this optical part 91 also becomes smooth. The intraocular lens 90 in a state appropriately folded in this way is released inside the eye by the release part 52 of the leading-end tip 5.

According to the injector 1 for an intraocular lens of the present embodiment explained above, the following such effects are exerted.

The lens holder 4 includes the base part 41, release-side guide part 42, and passing part 43. The first lens support part 92 is guided so as to run along the circumference of the optical part 91 by the release-side guide part 42. Since the first lens support part 92 thereby becomes a shape retained above the passing part 43, even when the optical part 91 starts to pass through the passing part 43, the first lens support part 92 will remain retained by the release-side guide part 42. Until immediately before the intraocular lens 90 is pushed out from the lens holder 4 to the side of the leading-end tip 5, it is possible to appropriately keep the shape of the first lens support part 92, and it is possible to much more safely perform insertion of the intraocular lens 90.

The lens holder 4 further includes the first through hole 62 and the rotating part 44. The release-side guide part 42 guides so that the first lens support part 92 at the setting end position runs along the circumference of the optical part 91, when the first projecting part 72 in a state sandwiched by the optical part 91 and first lens support part 92 moves from the setting initial position to the setting end position. It is thereby possible to reproducibly perform the setting operation that establishes a state appropriately keeping the shape of the first lens support part 92 according to a mechanical movement by way of rotation of the rotating part 44. When pushing the intraocular lens 90 out by the plunger 3, since it is sufficient to pull out the first projecting part 72 and second projecting part 73 at the setting end position from the first through hole 62 and second through hole 63, respectively, and push out by the plunger 3, it is possible to simply and steadily perform a series of operations from setting to release of the intraocular lens 90.

The release-side guide part 42 has a retaining part 83 that is arranged more to a side of the placement part 61 than a position at which the passing part 43 is arranged in the pushing direction PD of the plunger 3, and retains the first lens support part 92 at a position separated from the placement face at the setting initial position. Since the position of the first lens support part 92 at the setting initial position is already higher than the placement face, it is thereby possible to smoothly make movement of the first lens support part 92 to a position higher than the placement face. In addition, the entry of the first lens support part 92 to the passing part 43 can be effectively prevented.

The release-side guide part 42 has a sloped part 82 that is arranged at a position overlapping the passing part 43 in the thickness direction of the base part 41, and slopes to a side of the placement part 61 as approaching the passing part 43 in the thickness direction. Since entry of the first lens support part 92 to the passing part 43 is prevented by the sloped part 82 and contact between the first lens support part 92 and the release-side guide part 42 is more appropriately kept, it is thereby possible to effectively prevent a situation like the first lens support part 92 being separated from the release-side guide part 42 prior to the optical part 91 starting to pass through the passing part 43.

The release-side guide part 42 is arranged so as not to overlap with the leading-end portion of the plunger 3 when viewed in the pushing direction PD of the plunger 3. Since the plunger 3 will no longer interfere with the release-side guide part 42 during the pushing movement, it is possible to smoothly push out the intraocular lens 90 from the lens holder 4 to the release side.

The lens holder 4 includes the plunger-side guide part 45 that is arranged on the opposite side to the side that is the placement face side of the base part 41 at which the optical part 91 is placed, and releases the intraocular lens 90, and guides so that the second lens support part 93 at the setting end position runs along the circumference of the optical part 91. Also for the second lens support part 93 opposing the plunger 3 at the setting end position, due to being retained at an appropriate position by the plunger-side guide part 45, it is thereby possible to smoothly and accurately perform pushing out of the intraocular lens by the plunger 3.

Figure 9:
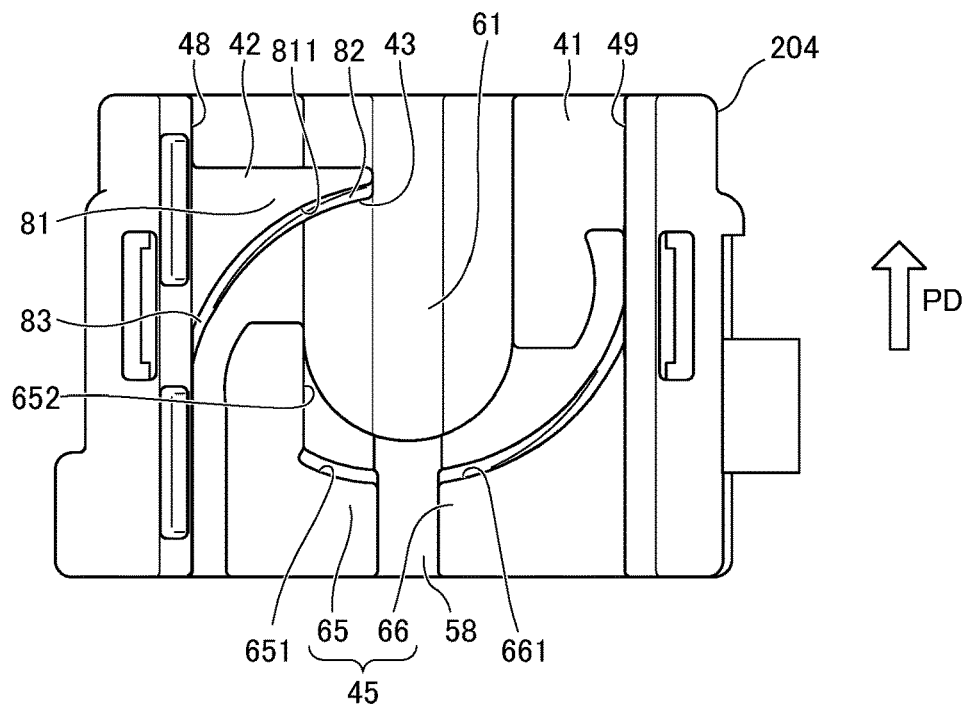
FIG. 9 is a plan view showing the inside of the lens holder of a second embodiment.
Figure 10:
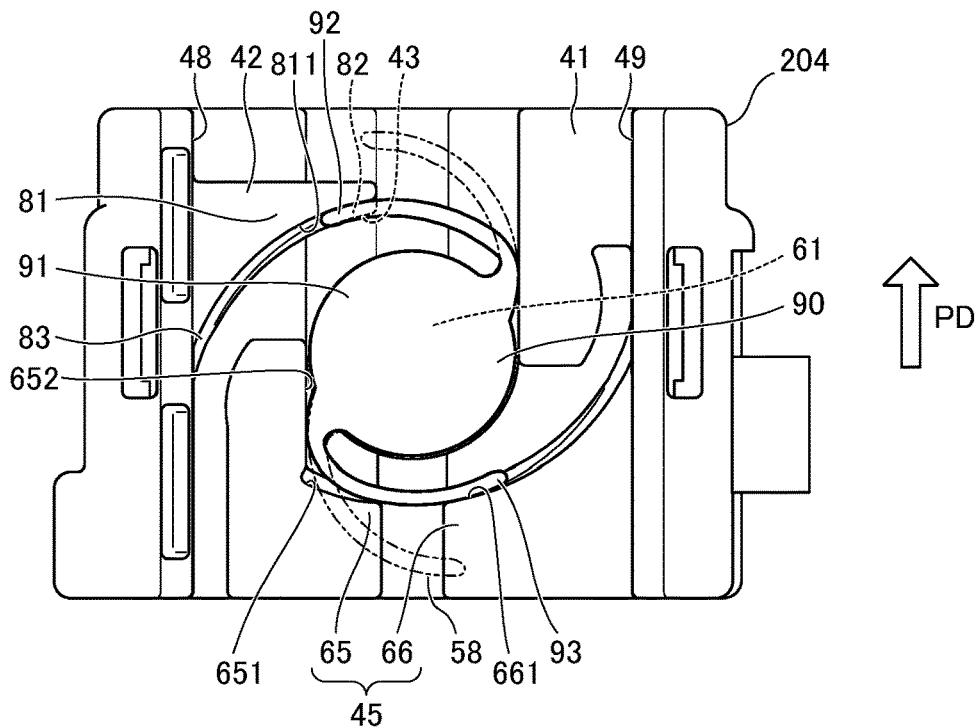
FIG. 10 is a plan view showing an aspect of the ocular lens being set in the lens holder of the second embodiment.

The injector 1 for an intraocular lens according to the first embodiment of the present invention is explained above. Next, an injector for an intraocular lens according to a second embodiment of the present invention will be explained. The injector 1 for an intraocular lens of the second embodiment differs in the points of not including the configurations of the rotating part 44, first through hole 62 and second through hole 63 possessed by the lens holder 4 of the first embodiment. FIG. 9 is a plan view showing the inside of a lens holder 204 of the second embodiment. FIG. 10 is a plan view showing an aspect of the intraocular lens 90 being set in the lens holder 204 of the second embodiment. It should be noted that the same reference symbols are assigned to configurations similar to the above-mentioned embodiment, and explanations thereof will be omitted.

For the operation of setting the intraocular lens 90 in the lens holder 204 of the second embodiment, an example of the intraocular lens 90 being set in the lens holder 204 by the hands of the user will be explained as one example.

In the second embodiment, as shown in FIG. 10, the intraocular lens 90 is set in the lens holder 204 so that the first lens support part 92 of the intraocular lens 90 is retained by the release-side guide part 42, and the second lens support part 93 is retained by the plunger-side guide part 45. More specifically, the intraocular lens 90 is placed in the lens holder 204 by making so as to hook the leading-end side of the first lens support part 92 at the curved face 811 of the release-side guide main body 81 and the sloped part 82. The first lens support part 92 thereby contacts the curved face 811 of the release-side guide main body 81 while being supported from below by the sloped part 82, and is retained above the passing part 43 by this friction force. As a result thereof, as shown in FIG. 10, the first lens support part 92 enters a state in which a leading end thereof reaches a position closer to the optical part 91 compared to a state not contacting with the release-side guide part 42, and is curved in a shape running along the outer circumference of the circular optical part 91, due to being retained by the release-side guide part 42.

In addition, the second lens support part 93 is placed in the lens holder 204 in a state contacting with the curved face 651 of the base-end side guide part 65 and the curved face 661 of the leading-end side guide part 66. With the second lens support part 93, as shown in FIG. 10, the leading end thereof thereby reaches a position closer to the optical part 91 compared to a state not contacting with the base-end side guide part 65 and leading-end side guide part 66, and is curved in a shape running along the outer circumference of the circular optical part 91.

As explained above, it is possible to retain the first lens support part 92 and second lens support part 93 in the lens holder 204 in an appropriate state also in the second embodiment. It should be noted that, although a configuration setting the intraocular lens 90 in the lens holder 204 by way of the hands of the user has been explained in the second embodiment, it is sufficient for the first lens support part 92 and second lens support part 93 of the intraocular lens 90 to be retained in an appropriate state inside the lens holder 204, and it is also possible to set the intraocular lens 90 at the position shown in FIG. 10 using another means such as a mechanical device.

Figure 11:
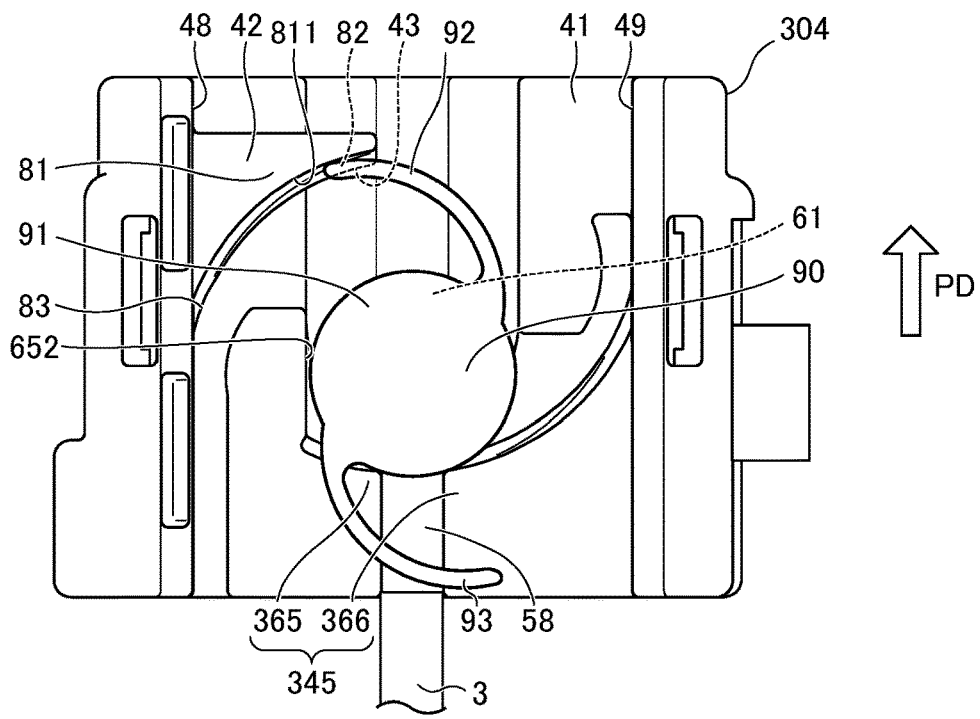
FIG. 11 is a plan view showing an aspect of the intraocular lens being set in a lens holder of a third embodiment.

Next, an injector for an intraocular lens according to a third embodiment of the present invention will be explained. The injector 1 for an intraocular lens of the third embodiment, similarly to the second embodiment, differs from the first embodiment in the point of not including the configurations of the rotating part 44, first through hole 62 and second through hole 63 possessed by the lens holder 4 of the first embodiment. FIG. 11 is a plan view showing an aspect of the intraocular lens 90 being set in a lens holder 304 of the third embodiment. It should be noted that the same reference symbols are assigned to configurations similar to the above-mentioned embodiments, and explanations thereof will be omitted.

The lens holder 304 of the third embodiment differs from the lens holder 204 of the second embodiment in the way of placing when initially placing the intraocular lens 90 in the lens holder 304. As shown in FIG. 11, the lens holder 304 of the third embodiment includes a plunger-side guide part 345 for deciding the position of the optical part 91 when the optical lens 90 is initially placed in the lens holder 304. The plunger-side guide part 345 is arranged at both sides of the plunger passing part 58, and includes a left-side guide part 365 arranged on the left side of the plunger passing part 58, and a right-side guide part 366 arranged on the right side.

Next, the operation of setting the intraocular lens 90 in the lens holder 304 by the user will be explained. The user places the intraocular lens 90 in the lens holder 304 so that parts on lateral sides of the optical part 91 contact the left-side guide part 365 and the right-side guide part 366, so as to enter the state shown in FIG. 11. Accompanying this, it is supported by making the leading end of the first lens support part 92 catch on the curved face 811 of the release-side guide main body 81 and the sloped part 82. At this moment, the first lens support part 92 is retained upwards from the passing part 43 by the release-side guide part 42; however, it is not a state curved to the side of the optical part 91. On the other hand, the second lens support part 93 is placed in a shape running on the top face of the plunger-side guide part 345. In this way, in the third embodiment, the positions of the optical part 91, first lens support part 92 and second lens support part 93 when initially placing the intraocular lens 90 in the lens holder 304 differ from the lens holder 204 of the second embodiment. According to the above operations, the setting of the intraocular lens 90 in the lens holder 304 prior to the insertion operation of the plunger 3 is completed. It should be noted that, in the third embodiment, establishing in a configuration that puts the first lens support part 92 in a state curved to some extent to the side of the optical part 91 when initially placing the intraocular lens 90 in the lens holder 304 is also possible.

Figure 12:
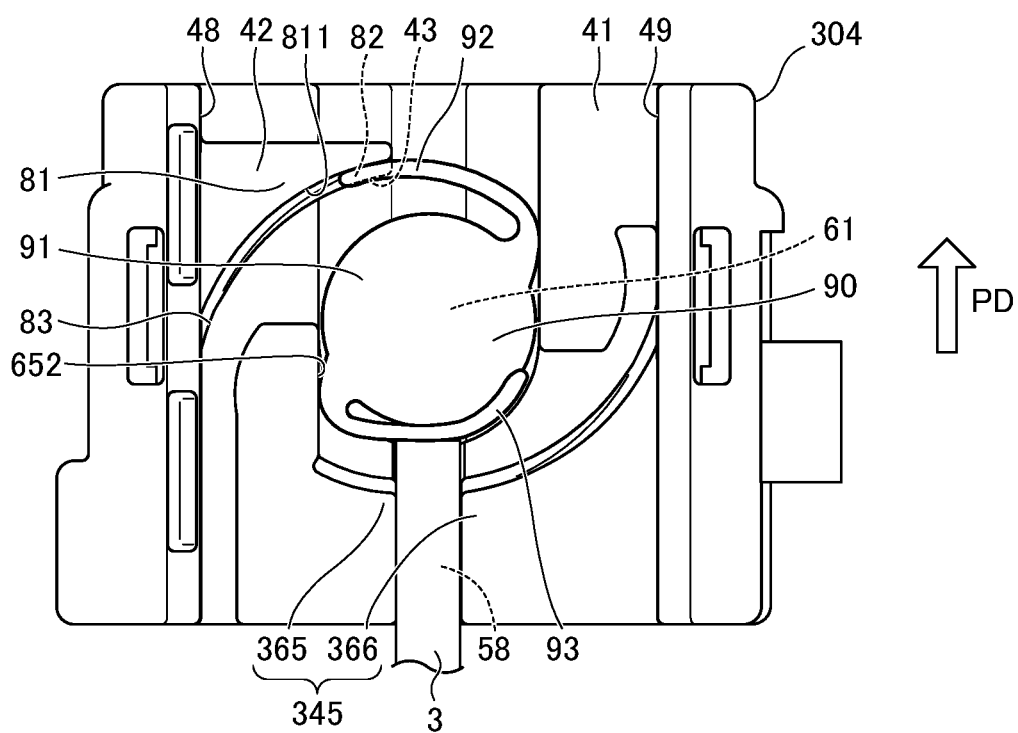
FIG. 12 is a plan view showing an aspect of the lens holder when the intraocular lens is pushed out of the third embodiment.

Next, the pushing operation of the plunger 3 will be explained. FIG. 12 is a plan view showing an aspect of the lens holder 304 when the intraocular lens 90 is pushed out in the third embodiment. As shown in FIG. 12, the intraocular lens 90 receiving the pressure force of the plunger 3 enters a state in which the second lens part 93 is greatly curved to the side of the optical part 91 by the plunger 3, and moves to the release side in this state. The leading-end side of the first lens support part 92 also enters a state curved to the side of the optical part 91 by the release-side guide part 42, accompanying the movement of the intraocular lens 90 to the release side (state of FIG. 12). In this way, in the course of the insertion operation of the plunger 3, with the first lens support part 92, the leading end thereof reaches a position closer to the optical part 91 due to the release-side guide part 42, compared to a state not contacting with the release-side guide part 42, and enters a state curved in a shape running along the outer circumference of the circular optical part 91. On the other hand, with the second lens support part 93, the leading end thereof reaches a position closer to the optical part 91 due to the plunger 3, and enters a state curved in a shape running along the outer circumference of the circular optical part 91.

When further advancing to the release side from the state of FIG. 12, the optical part 91 starts to pass through the passing part 43. As mentioned above, the first lens support part 92 is retained upwards from the passing part 43 by the release-side guide part 42; therefore, the first lens support part 92 remains in contact with the curved face 811 of the release-side guide main body 81 and the sloped part 82 without passing through the passing part 43 also in the third embodiment. When the intraocular lens 90 moves further to the release side, a portion of the first lens support part 92 contacting the release-side guide part 42 moves from the base-end side to the leading-end side while deforming further, and eventually separates from the release-side guide part 42. Movement of the intraocular lens 90 thereafter is the same as the first embodiment.

As explained above, it is possible to perform the insertion operation of the plunger 3 while retaining the first lens support part 92 and second lens support part 93 in appropriate states by the lens holder 304, also in the third embodiment.

Figure 13:
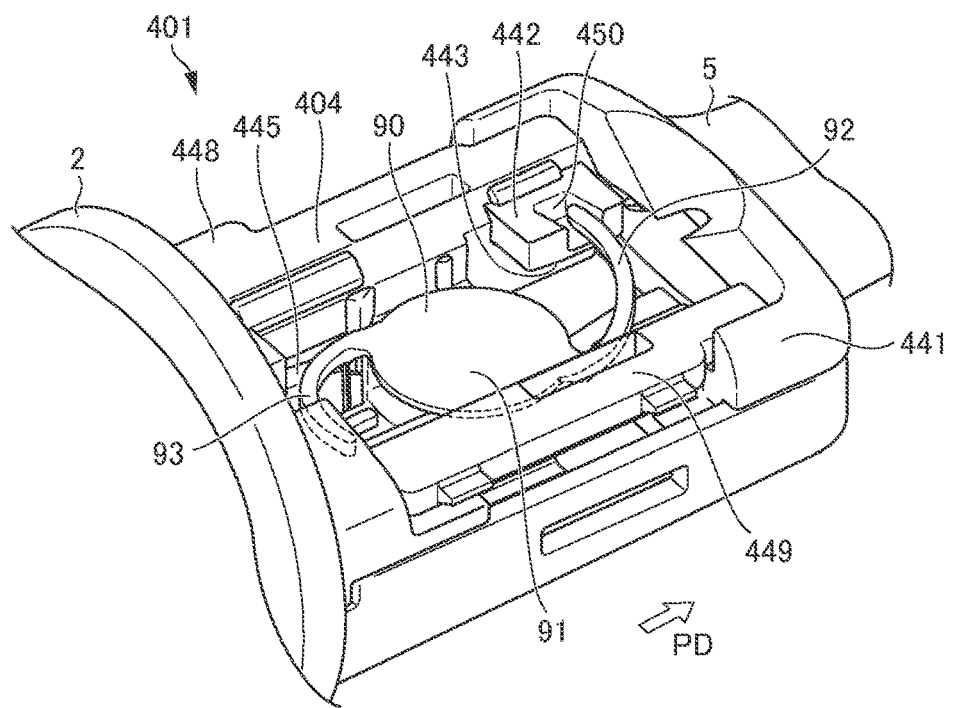
FIG. 13 is a perspective view showing an aspect of an intraocular lens being set in a lens holder of a fourth embodiment.
Figure 14:
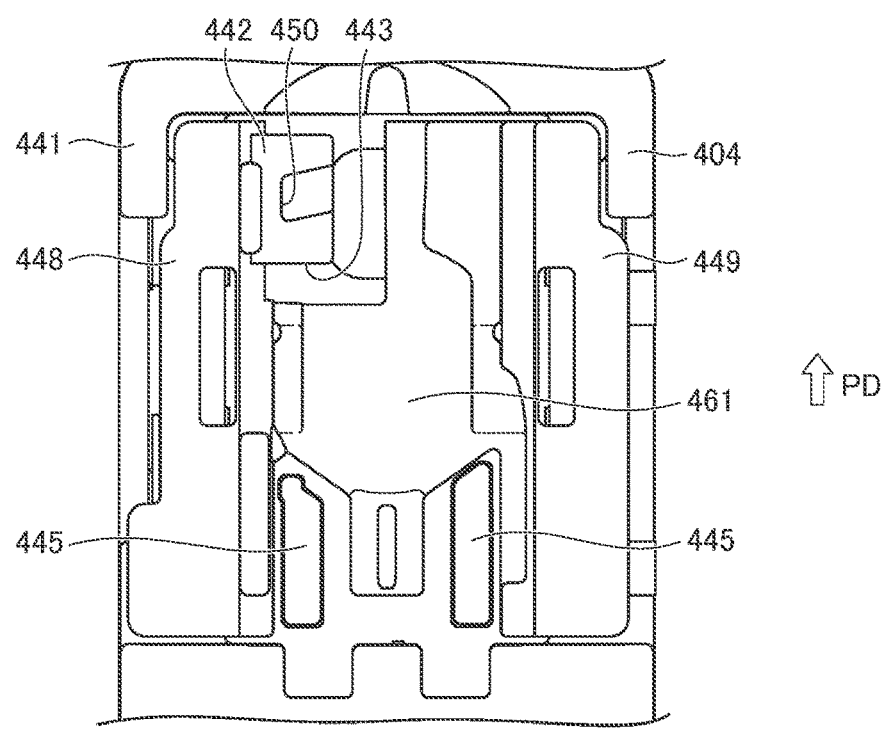
FIG. 14 is a plan view showing the inside of the lens holder of the fourth embodiment.

Next, an injector for an intraocular lens according to a fourth embodiment of the present invention will be explained. An injector 401 for an intraocular lens of the fourth embodiment includes a lens holder 404 of a different configuration from the lens holders of the above-mentioned embodiments. FIG. 13 is a perspective view showing an aspect of the intraocular lens 90 being set in the lens holder 404 of the fourth embodiment. FIG. 14 is a plan view showing inside of the lens holder 404 of the fourth embodiment.

As shown in FIG. 13, the lens holder 404 of the fourth embodiment includes a base part 441, a release-side guide part 442, a passing part 443, a plunger-side guide part 445, and a cover 46 (omitted from illustration in FIGS. 13 and 14).

The base part 441 is formed in a substantially plate shape, and includes a placement part 461, and wall parts 448 and 449. As shown in FIG. 14, the placement part 461 is a portion at which the optical part 91 of the intraocular lens 90 set in the lens holder 404 is placed, and is arranged at the center of the base part 441. In addition, at a main body 2 side of the base part 441, the plunger passing part 58 (omitted from illustration) for allowing the plunger 3 to pass through is formed. The wall part 448 is arranged on the left side (one side) of the base part 441, and the wall part 449 is arranged on the right side (other side).

The release-side guide part 442 is arranged on a release side of the base part 441, which is a top face of the base part 441. The release-side guide part 442 of the fourth embodiment projects in the left/right direction from an inside top part of the wall part 448, and is formed in a cubic shape. In addition, the release-side guide part 442 is arranged so as not to overlap with the leading-end portion of the plunger 3 when viewed in the pushing direction of the plunger 3, also in the fourth embodiment.

A concave part 450 for accommodating the leading end of the first lens support part 92 is formed in the release-side guide part 442. The concave part 450 is formed from the lateral face that faces in the left/right direction of the release-side guide part 442 to the top face.

The passing part 443 is arranged in a channel through which the optical part 91 of the intraocular lens 90 passes, which is below the release-side guide part 442. The passing part 443 of the fourth embodiment is configured so that the left side of the optical part 91 passes through the passing part 43 when the intraocular lens 90 moves from the lens holder 404 to the leading-end tip 5 (refer to FIG. 16). As shown in FIG. 13, the passing part 443 of the fourth embodiment is formed in a gap between the bottom face of the release-side guide part 442 and the top face of the base part 441. In this way, the release-side guide part 442 is formed above the passing part 443; therefore, the bottom face of the concave part 450 formed in the release-side guide part 442 is at a position higher than the passing part 443.

Two of the plunger-side guide parts 445 are arranged at a main body 2 side of the base part 441. The two plunger-side guide parts 445 are aligned in the left/right direction, and both are formed in wall shapes projecting upwards from the top face of the base part 441. The two plunger-side guide parts 445 support the second lens support part 93 of the intraocular lens 90 from below by the top faces thereof.

Figure 15:
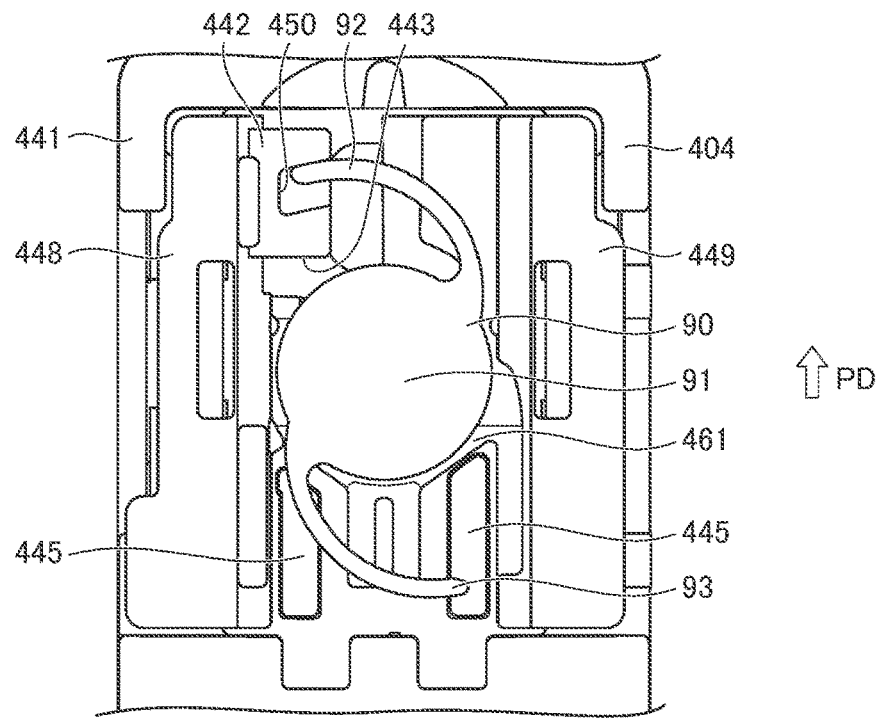
FIG. 15 is a plan view showing an aspect of the intraocular lens being set in the lens holder of the fourth embodiment.

The main configuration of the lens holder 404 of the fourth embodiment is as above. Next, operations to set the intraocular lens 90 in the lens holder 404 by the user will be explained. FIG. 15 is a plan view showing an aspect of the intraocular lens 90 being set in the lens holder 404 of the fourth embodiment.

The user places the optical part 91 of the intraocular lens 90 on the placement part 461, and places the leading end of the first lens support part 92 in a concave part 450 of the release-side guide part 442, so as to establish the state shown in FIG. 15. The position of the concave part 450 is established so that the position of the first lens support part 92 will be appropriate. Therefore, the user can set the intraocular lens 90 appropriately and easily in the lens holder 404 by providing the concave part 450 as a landmark to place the first lens support part 92. Also for the second lens support part 93, the position thereof is intuitively decided by the first lens support part 92 being appropriately set, and is a shape supported on the top face of the plunger-side guide part 445.

As mentioned above, the concave part 450 supporting the first lens support part 92 is positioned upwards from the passing part 443; therefore, the leading-end side of the first lens support part 92 is retained upwards from the passing part 443. According to the above operations, setting of the intraocular lens 90 to the lens holder 404 is completed prior to the insertion operation by the plunger 3.

Figure 16:
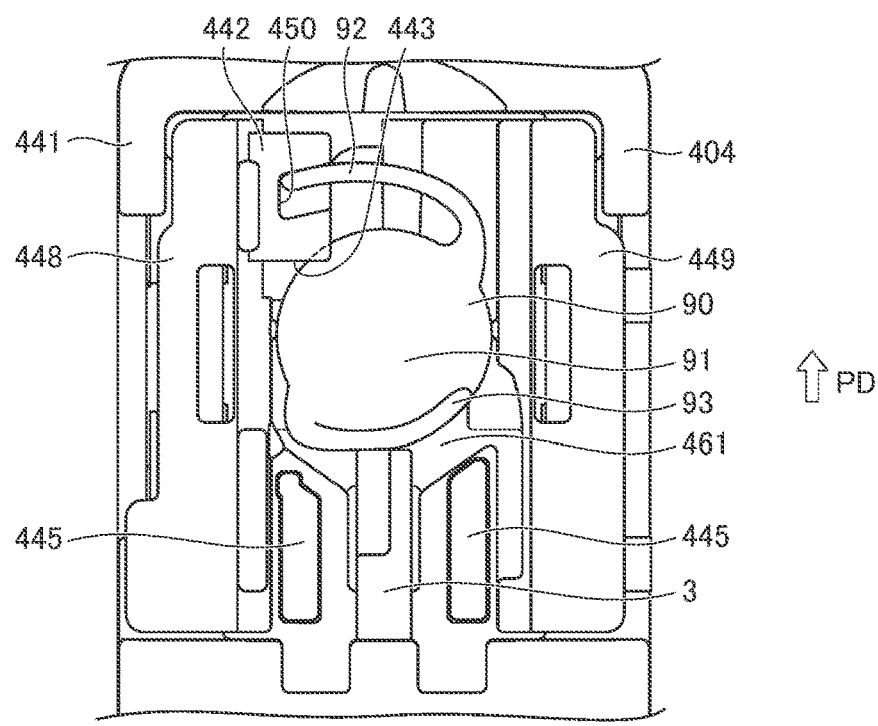
FIG. 16 is a plan view showing an aspect of the lens holder of the fourth embodiment when the intraocular lens is pushed out.

Next, the pushing operation of the plunger 3 will be explained. FIG. 16 is a plan view showing an aspect of the lens holder 404 when the intraocular lens 90 of the fourth embodiment is pushed out.

With the intraocular lens 90 receiving the pressure force of the plunger 3, the second lens support part 93 thereof is curved greatly to the side of the optical part 91 by the plunger 3. It thereby enters a state such that a part of the second lens support part 93 is positioned above the optical part 91, and moves to the release side in this state. As shown in FIG. 16, the leading-end side of the first lens support part 92 enters a state curved to the optical part 91 side by the inner wall of the concave part 450 of the release-side guide part 442 accompanying the movement of the intraocular lens 90 to the release side. In this way, in the course of the insertion operation by the plunger 3, due to the release-side guide part 442, a leading end of the first lens support part 92 reaches a position closer to the optical part 91, compared to a state not contacting with the release-side guide part 442, and enters a state curved in a shape running along the outer circumference of the circular optical part 91.

As shown in FIG. 16, when the intraocular lens 90 advances to the release side, the optical part 91 starts to pass through the passing part 443. As mentioned above, the first lens support part 92 is retained upwards from the passing part 443 by the release-side guide part 442; therefore, it will remain retained above the passing part 43 by the concave part 450 of the release-side guide part 442 without passing through the passing part 43 also during movement of the intraocular lens 90 of the fourth embodiment. When the intraocular lens 90 moves further to the release side from the state shown in FIG. 16, the contact site of the concave part 450 with the first lens support part 92 gradually moves in a direction separating from the concave part 450, and the first lens support part 92 eventually separates from the concave part 450. At this moment, the intraocular lens 90 sufficiently advances to the release side; therefore, the intraocular lens 90 moves inside of the leading-end tip 5 in a state appropriately retaining the position of the first lens support part 92. The movement of the intraocular lens 90 thereafter is the same as the first embodiment.

According to the injector 401 for an intraocular lens of the fourth embodiment explained above, the following such effects are exerted.

The concave part 450 accommodating the leading end of the first lens support part 92 is formed in the release-side guide part 442. It is thereby possible to appropriately and easily set the intraocular lens 90 in the lens holder 404 by making the leading end of the first lens support part 92 be accommodated in the concave part 450. In addition, it is possible to effectively prevent penetration of the first lens support part 92 into the passing part 43.

The release-side guide part 442 retains the first lens support part 92 upwards from the passing part 443 by the concave part 450. Since the first lens support part 92 comes to be appropriately folded above the optical part 91 in the insertion operation by the plunger 3, it is thereby possible to make the operation for sending the intraocular lens 90 to the leading-end tip 5 side more stable.

Although the respective preferred embodiments of injectors for intraocular lens of the present invention have been explained above, the present invention is not to be limited to the aforementioned embodiments, and modifications are possible where appropriate.

It is also possible to modify the configuration of the release-side guide part 42 in the above-mentioned embodiments as follows. For example, it is also possible to form so as to curve the shape of the sloped part 82 of the release-side guide part 42, and modify to a configuration projecting step-wise from the curved face 811 of the release-side guide main body 81. In addition, it is also possible configure the curved face 811 of the release-side guide main body 81 so as to slope to the side of the placement part 61 as approaching upwards. In addition, the top face of the retaining part 83 of the present embodiment is configured as an upslope facing the release side; however, it is also possible to configure by making the top face thereof substantially parallel with the placement face, and setting at substantially the same height as the passing part 43. In addition, it is also possible to make a configuration omitting the sloped part 82 and retaining part 83 from the configuration of the release-side guide part 42. Furthermore, it is possible to appropriately modify the configuration in which the leading-end side of the release-side guide part 42 is positioned ahead of the through channel of the plunger 3 to match the shape of the plunger 3. For example, it is also possible to make a configuration such that the plunger 3 passes below the leading-end portion of the release-side guide part 42, without overlapping with the leading-end side thereof when viewed in the pushing direction, despite the leading-end side of the release-side guide part 42 overlapping with the through channel of the plunger 3 in a plan view.

The plunger-side guide part 45 of the above-mentioned embodiments is disposed adjacent to the plunger passing part 58; however, it is also possible to dispose to be separated from the plunger passing part 58.

In the above-mentioned embodiments, a configuration whereby the user of the injector 1 for an intraocular lens sets the intraocular lens 90 in the lens holder 4 is explained; however, the present invention can also be applied to an injector for an intraocular lens of so-called preload type of a configuration whereby the intraocular lens is set in the lens holder in advance. More specifically, with the injector for an intraocular lens of preload type, the intraocular lens is accommodated in the lens holder in advance in the state of the setting initial position explained in the above-mentioned embodiments. When the user uses the injector for an intraocular lens, the rotating part is made to move from the setting initial position to the setting end position. The intraocular lens moves to the setting end position, and enters a state in which the first lens support part and second lens support part are retained at appropriate positions. The intraocular lens is pushed out by the plunger in this state and released intraocularly. In this way, with an injector for an intraocular lens of preload type made by adopting the present invention, the first lens support part and second lens support part come to be guided to the setting end position immediately before the insertion operation. Therefore, compared to the configuration accommodating the first lens support part and second lens support part in the lens holder in a deformed state for a long time, it is possible to effectively reduce the load acting on the first lens support part and second lens support part.

In the above-mentioned embodiments, configurations in which the lens holder 4 is fixed to the main body 2 are explained; however, it is also possible to apply the present invention to an injector for an intraocular lens of a configuration that establishes a cartridge-type lens holder as a separate component from the main body, and installs the lens holder in the main body during use of the injector for intraocular lens. An example of a cartridge-type lens holder will be explained. The cartridge-type lens holder has an engaging part that can install in the main body of the injector for an intraocular lens, and is configured so that the insides of the leading-end tip and lens holder are in communication by installing to the main body by way of this engaging part. This lens holder is of preload type, and the intraocular lens is set in advance in a state of the setting initial position of the above-mentioned embodiments. When the user uses the injector for an intraocular lens, the lens holder is taken out of a predetermined container, and installed in the main body of the injector for an intraocular lens. In a state in which the lens holder is installed in the main body of the injector for an intraocular lens, the rotating part is made to move from the setting initial position to the setting end position. The intraocular lens thereby moves to the setting end position, and enters a state in which the first lens support part and the second lens support part are retained at appropriate positions. With this configuration, it is possible to effectively reduce the load on the first lens support part and second lens support part. It should be noted that the leading-end tip is configured as a separate component from the main body similarly to the lens holder, and it is possible to make a configuration that installs in the main body along with the lens holder upon use. In addition, as the above-mentioned cartridge-type lens holder, there is a type, etc. that stores an intraocular lens for every lens holder in a container filled with a predetermined solution, and the user uses the lens holder by removing from the container upon use of the injector for an intraocular lens.

In the above-mentioned embodiments, a single-piece type is explained as an example of the intraocular lens 90; however, the present invention can also be applied to intraocular lenses of other configurations that include support parts, such as of three-piece type.

The release-side guide part 442 of the fourth embodiment can be appropriately modified in the configuration thereof. For example, it is possible to modify the shape of the concave part 450, and make a configuration sloping the bottom face of the concave part 450. In addition, it is also possible to modify the plunger-side guide part 445 of the fourth embodiment to a configuration guiding the second lens support part 93 so as to run along the circumference of the optical part 91 (configuration similar to plunger-side guide part 45 of first embodiment).

EXPLANATION OF REFERENCE NUMERALS 1 injector for an intraocular lens
3 plunger
4 lens holder
41 base part
42 release-side guide part
43 passing part
44 rotating part
45 plunger-side guide part
61 placement part
62 first through hole
63 second through hole
72 first projecting part
73 second projecting part
82 sloped part
83 retaining part
90 intraocular lens
91 optical part
92 first lens support part
93 second lens support part
204 lens holder
304 lens holder
401 injector for an intraocular lens
404 lens holder
441 base part
442 release-side guide part
443 passing part
450 concave part
461 placement part

The invention claimed is:
1. An injector for an intraocular lens having an optical part and a lens support part extending from the optical part, the injector comprising:
a lens holder comprising:
a base part having a placement part adapted to allow the optical part of the intraocular lens to be placed on the placement part,
a release-side guide part that is disposed at a placement face side of the base part on which the optical part is placed, which is a side releasing the intraocular lens, and guides the lens support part so as to run along a circumference of the optical part, and
a passing part formed between the placement part and a bottom face of the release-side guide part to allow the optical part to pass therethrough; and
a plunger adapted to push out and release the intraocular lens that is set in the lens holder,
wherein the lens holder further comprises:
a through hole that is formed at a periphery of the placement part of the base part so as to run along an outer circumference of the optical part; and
a rotating part having a basal part and a projecting part that projects from the basal part, being disposed on a surface opposite to the placement part of the base part so that the projecting part can be inserted and removed from the through hole, and being able to rotate so that the projecting part moves along the through hole, wherein the through hole is formed so that at least a part thereof is disposed between the placement part and the release-side guide part, and when viewed in a pushing direction of the plunger, the projecting part inserted in the through hole can move from a setting initial position overlapping with the release-side guide part until a setting end position not overlapping with the release-side guide part, and wherein the release-side guide part,
when the projecting part in a state sandwiched between the optical part and the lens support part moves from the setting initial position to the setting end position, guides the lens support part at the setting end position so as to run along the circumference of the optical part.

2. The injector for an intraocular lens according to claim 1, wherein a concave part that accommodates a leading end of the lens support part is formed in the release-side guide part.

3. The injector for an intraocular lens according to claim 2,
wherein the release-side guide part retains the lens support part upwards from the passing part by way of the concave part.

4. The injector for an intraocular lens according to claim 1,
wherein the release-side guide part has a projection that is disposed more to a side of the placement part than a position at which the passing part is disposed in the pushing direction of the plunger, and retains the lens support part at a position separated from the placement part at the setting initial position.

5. The injector for an intraocular lens according to claim 1,
wherein the release-side guide part has a sloped part that is disposed at a position overlapping the passing part in a thickness direction of the base part, and slopes to a side of the placement part as approaching the passing part in the thickness direction.

6. The injector for an intraocular lens according to claim 1,
wherein the release-side guide part is disposed so as not to overlap with a leading-end portion of the plunger when viewed in the pushing direction of the plunger.

7. The injector for an intraocular lens according to claim 1,
wherein the intraocular lens has a second support part that is disposed so as to be point symmetrical with a center of the optical part as the center of symmetry relative to the lens support part, and
wherein the lens holder further includes a plunger-side guide part that is disposed at an opposite side to the placement face side of the base part on which the optical part is placed, which is the side releasing the intraocular lens, and guides the second support part so as to run along the circumference of the optical part.

* * * * *